United States Patent [19]

Pifferi et al.

[11] 4,041,048

[45] Aug. 9, 1977

[54] 3,2-BENZOXAZEPINE DERIVATIVES

[75] Inventors: Giorgio Pifferi, Milan; Amedeo Omodei-Salé, Pavia; Pietro Consonni, Milan, all of Italy

[73] Assignee: Gruppo Lepetit S.p.A., Milan, Italy

[21] Appl. No.: 523,790

[22] Filed: Nov. 14, 1974

Related U.S. Application Data

[63] Continuation-in-part of Ser. No. 234,336, March 13, 1972, abandoned.

[30] Foreign Application Priority Data

Mar. 18, 1971 Italy .................................. 21930/71
Jan. 20, 1972 Italy .................................. 19575/72

[51] Int. Cl.$^2$ ......................................... C07D 267/02
[52] U.S. Cl. .................................... 260/333; 424/244;
424/248.54; 424/267; 260/243.3; 260/268 BC;
260/293.58; 260/326.34; 260/471 C; 260/488
CD; 260/618 D
[58] Field of Search ........................................ 260/333

[56] References Cited

U.S. PATENT DOCUMENTS 2,807,628 9/1957 Belleau .................................. 260/333
3,660,387 5/1972 Piffert et al. ......................... 260/244

OTHER PUBLICATIONS

Pifferi et al., J. Heterocyclic chem., vol. 8, pp. 911–918 (12/1971).
Pifferi et al., J. Med. Chem., vol. 12, pp. 261–266 (1969).

Primary Examiner—Henry R. Jiles
Assistant Examiner—R. W. Ramsuer
Attorney, Agent, or Firm—Theodore Post; C. Kenneth Bjork

[57] ABSTRACT 3,2-Benzoxazepines of the formula

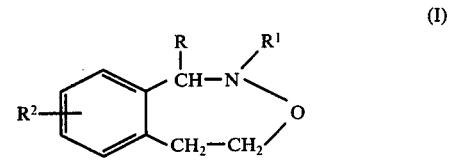

(I)

and their preparation. In formula (I), R respesents hydrogen or lower alkyl; $R^1$ represents hydrogen, lower alkyl, lower alkenyl, hydroxy-lower alkyl, carbamyloxy-lower alkyl, acyl, amidino, carbamyl, mono- or di-substituted carbamyl; $R^2$ may be in position 7 or 8 of the benzoxazepine ring and represents hydrogen, nitro, amino, acetamino or halo. The compounds are prepared by reacting 1,2,4,5-tetrahydro-3,2-benzoxazepine with a reactant which reacts with a secondary amino group to give substitution in the 2-position. The compounds have anti-inflammatory and central nervous system activity.

7 Claims, No Drawings

3,2-BENZOXAZEPINE DERIVATIVES

CROSS-REFERENCE TO RELATED APPLICATION

This application is a continuation-in-part of U.S. patent application Ser. No. 234,336 filed Mar. 13, 1972, now abandoned.

SUMMARY OF THE INVENTION

This invention relates to a new class of 3,2-benzoxazepines of the formula

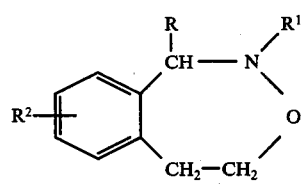

and to their preparation. In formula (I), R represents hydrogen or lower alkyl, $R^1$ represents a member selected from the group consisting of hydrogen, lower alkyl, lower alkenyl, hydroxy-lower alkyl, carbamyloxy-lower alkyl, acyl, amidino, carbamyl, mono- or di-substituted carbamyl, $R^2$ may be in position 7 or 8 of the benzoxazepine ring and represents hydrogen, nitro, amino, acetamino or halo. As used in the specification and claims, the terms "lower alkyl", "hydroxy-lower alkyl" and "lower alkoxy" designate groups having from 1 to 4 carbon atoms such as, for example, methyl, ethyl, propyl and butyl; hydroxymethyl, hydroxyethyl, hydroxypropyl and hydroxybutyl; and methoxy, ethoxy, propoxy and butoxy, respectively; and the term "lower alkenyl" is employed to mean ethylenic unsaturated groups having from 3 to 5 carbon atoms. The term "acyl" designates a 2 to 5 carbon acyl group derived from alkanoic and alkenoic acids as well as from benzoic and substituted benzoic acids having halo, nitro, amino or lower alkoxy substituents, and from the heterocyclic acids 1-piperidinecarboxylic acid, 4-morpholinecarboxylic acid, 1-pyrrolidinecarboxylic acid and 4 methyl-1-piperazinecarboxylic acid. The term "substituted carbamyl" designates carbamyl having lower alkyl, hydroxy-lower alkyl, lower alkenyl or phenyl substituents on the carbamyl group.

A preferred group of compounds comprises those derivatives of formula (I) wherein R is hydrogen or methyl, $R^1$ is hydrogen, lower alkyl, carbamyl, mono- or di-lower alkyl carbamyl, carbamyloxyethyl, 2 to 4 carbon alkanoyl, 1-piperidinylcarbonyl and 4-morpholinylcarbonyl and $R^2$ is hydrogen, nitro, amino, acetamino or chloro.

A most preferred group of compounds comprises those of formula (I) wherein R is hydrogen or methyl, $R^1$ is hydrgen, methyl, carbamyl, methylcarbamyl, ethylcarbamyl, dimethylcarbamyl, diethylcarbamyl, carbamyloxyethyl, acetyl, 1-piperidinylcarbonyl or 4-morpholinylcarbonyl and $R^2$ is hydrogen.

The starting material for the preparation of the novel 3,2-benzoxazepines is the basic seven-membered ring fused with the benzene nucleus. It is prepared by the following steps. The N,O-disubstituted hydroxylamine corresponding to following formula (II) is cyclized by treatment with an equimolar or substantially equimolar proportion of a strong base, e.g., an alkali metal hydroxide, advantageously at room temperature, according to the following reaction scheme:

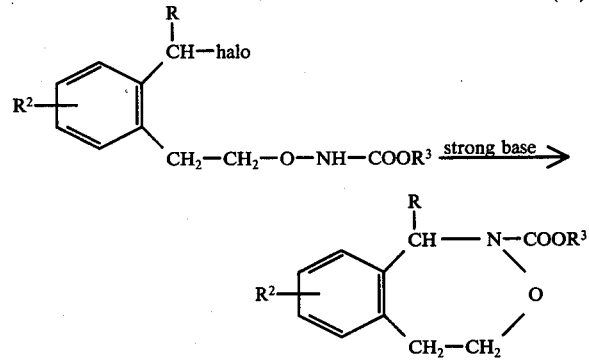

wherein R and $R^2$ have the significance previously indicated and $R^3$ is a lower alkyl or a phenyl lower alkyl group, to give the corresponding 1,2,4,5-tetrahydro-3,2-benzoxazepine of formula (III). The ring closure reaction is effected in a suitable organic solvent as reaction medium, advantageously one of the lower alkanols.

The starting material represented by formula (II) is prepared by reacting an alkali metal salt of a hydroxyurethane with a phenethyl halide having in the ortho-position of the benzene ring a suitable substituent which can be readily transformed into a 1-halo-lower alkyl group, halo or halide representing chloro or bromo or chloride or bromide, respectively. For instance, when the compound of formula (II) wherein R is hydrogen is desired, (o-acetoxymethyl)phenethyl bromide, obtained by hydrogenation of o-(2-bromoethyl)benzaldehyde, is used. The resulting O-(o-acetoxymethyl)phenethyl-N-carbethoxyhydroxylamine is subsequently transformed into the respective hydroxymethyl compound by hydrolytic cleavage with an alkali metal hydroxide. Treatment with a hydrogen halide affords the compound of formula (II), wherein R is hydrogen.

In some instances, protection of the o-(1-hydroxyalkyl) group on the phenethyl halide through acylation is not required. In particular, when R is lower alkyl, and alkali metal salt of a hydroxyurethane is condensed directly with an o-(1-hydroxyalkyl)phenethyl halide to give a compound of the formula

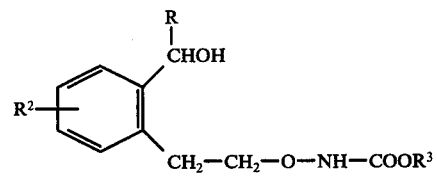

wherein R is lower alkyl, $R^2$ has the same meaning as before and $R^3$ is lower alkyl or phenyl lower alkyl. These compounds are then easily transformed into the compounds of formula (II).

The 2-carboalkoxy radical of a 2-carboalkoxy-1,2,4,5-tetrahydro-3,2-benzoxazepine is split off by hydrolytic cleavage to give the 2-unsubstituted 3,2-benzoxazepine compound which, in turn, is transformed by simple chemical reactions into the other inventive compounds encompassed by formula (I). Thus, the compounds wherein $R^1$ is a lower alkyl or a lower alkenyl group are obtained by reaction of 1,2,4,5-tetrahydro-3,2-benzoxazepine with a lower alkyl or a lower alkenyl halide, or in the case wherein R¹ is a methyl group, by heating with a mixture of formic acid and formaldehyde. Compounds wherein R¹ is acyl are prepared by acylating the nitrogen atom in position 2 with conventional reagents such as an acyl halide in the presence of a tertiary nitrogen base or a carboxy acid anhydride. The secondary amino group of the seven-membered ring can also be reacted with other reagents capable of transformation into other end compounds of formula (I). For instance, when R¹ is carbamyloxy lower alkyl, a lower alkylene oxide (e.g., ethylene oxide) can be used in the first step and the resulting 2-hydroxyalkyl radical can be converted into the carbamyloxyalkyl group by treatment with a mixture of sodium cyanate and hydrogen chloride in a suitable solvent. The latter method may be followed to prepare 2-carbamyl-1,2,4,5-tetrahydro-3,2-benzoxazepine starting with the 2-unsubstituted tetrahydro-3,2-benzoxazepine.

The inventive compounds of formula (I) wherein R¹ is a disubstituted carbamyl group are preferably prepared by reacting the corresponding disubstituted carbamyl halide with 1,2,4,5-tetrahydro-3,2-benzoxazepine in the presence of a strong organic base, e.g., triethylamine. Alternatively, these compounds can be prepared by reacting an appropriate corresponding 1,2,4,5-tetrahydro-3,2-benzoxazepine-2-carbonyl chloride with an appropriate corresponding amine. When the amine is selected from a nitrogen-containing heterocyclic compound such as morpholine or piperidine, the resulting compound is one wherein R¹ represents heterocyclic acyl. Other known chemical reactants can be used to substitute in position 2 a desired substituent, such as, for example, cyanamide when the amidino group is desired and formaldehyde when the hydroxymethyl group is desired.

In a preferred method for effecting ring closure of compounds of formula (II), a lower alkanol solution containing an equimolecular amount of an alkali metal hydroxide is added dropwise at room temperature to an alcoholic solution of the hydroxylamine derivative of formula (II). The reaction mixture is then continuously stirred for a period of time varying from about 2 to about 4 hours. The reaction proceeds with the formation of a hydrohalide which forms a metal salt with the alkali metal hydroxide present. After stirring, the resulting solution is allowed to stand for several hours at room temperature and then is evaporated in vacuo. The residue is taken up with diethyl ether and the inorganic precipitate is filtered off. The filtrate is then evaporated and the residue is distilled under vacuum, discarding the first fractions when R is lower alkyl since they may contain some impurities such as (vinyl-substituted phenethyl)hydroxylamine derivatives. The residue from the distillation may contain other impurities deriving from an intermolecular cyclization.

When compounds having a substituent in the aromatic ring are desired, one uses as a starting material a compound of formula (II) wherein R² has the indicated significance, such as, for example, chloro, nitro or acetamino.

An alternative method for preparing these compounds involves nitrating a 2-acyl-3,2-benzoxazepine such as, for example, 2-acetyl-1-methyl-1,2,4,5-tetrahydro-3,2-benzoxazepine, separating the two isomers having the nitro group in positions 7 and 8, catalytically hydrogenating the nitro group of both isomers, substituting the so-obtained amino group with halogen via Sandmeyer's reaction, and splitting off the 2-acyl group by acid hydrolysis. The latter step may be effected also with the foregoing 7- or 8-nitro derivative to give the corresponding 3-unsubstituted benzoxazepine. Of course, all reactions suitable for the substitution of new groups in position 2 may be carried out with these compounds. In the instance wherein the end compound contains an amino group in position 7 or 8 and a radical which is different from acetyl in position 2, it is preferable to carry out the hydrolysis of the acetyl group in a first stage, and then to introduce the new substituent in position 2 by way of the previously mentioned reactions, finally hydrogenating the nitro group.

In a preferred embodiment of the invention, the nitration of a 2-acetyl-1,2,3,4-tetrahydro-3,2-benzoxazepine compound is carried out by using as nitrating agent a solution of 1 to 1.5 equimolecular proportion of KNO₃ in concentrated sulfuric acid at a temperature between about −5° and about +5° C. The separation of the two isomeric nitro derivatives is effected by fractional crystallization from diisopropyl ether. The catalytic hydrogenation of the nitro groups is carried out at room temperature using 5 percent palladiated charcoal as catalyst. The other reaction steps are carried out according to general methods which are well known to the art skilled.

The following additional description and examples further describe the invention and the manner and process of making and using it to enable the art skilled to make and use the same and set forth the best mode contemplated by the inventors of carrying out the invention.

EXAMPLE 1

2-Carbethoxy-1,2,4,5-tetrahydro-3,2-benzoxazepine

A solution of 19.8 g. of 85 percent potassium hydroxide (0.3 mole) in 800 ml. of ethanol was added dropwise at room temperature to a stirred solution of 90 g. (0.3 mole) of O-[(o-bromomethyl)phenethyl]-N-carbethoxyhydroxylamine in 2800 ml. of ethanol. Stirring was continued for four hours, then the mixture was evaporated in vacuo to dryness. The residue was taken up with diethyl ether and the inorganic salts were filtered off. The filtrate was evaporated and the residue distilled, collecting the fraction boiling at 140°–145°C/0.2 mm Hg. Yield 53.4 g. (82%).

Analysis: Calculated for $C_{12}H_{15}NO_3$: C, 65.14; H, 6.83; N, 6.33. Found: C, 64.89; H, 6.46; N, 6.50.

EXAMPLE 2: 1,2,4,5-Tetrahydro-3,2-benzoxazepine

A solution of 22.5 g. (0.34 mole) of potassium hydroxide in 30 ml. of water was added under stirring to a solution of 49.4 g. (0.22 mole) of 2-carbethoxy-1,2,4,5-tetrahydro-3,2-benzoxazepine in 300 ml. of ethanol. The solution was refluxed for four hours and the solvent removed in vacuo. The residue was taken up with diethyl ether, washed with water and dried over anhydrous sodium sulfate. Evaporation gave a residue which was crystallized from diisopropyl ether to yield 28.8 g. (86.8%) of 1,2,4,5-tetrahydro-3,2-benzoxazepine melting at 87°–88° C. The hydrochloride, prepared by reaction of the latter with a solution of hydrogen chloride in diethyl ether, melted at 190°–192° C.

Analysis: Calculated for $C_9H_{11}NO$: C, 72.45; H, 7.43; N, 9.39. Found: C, 72.36; H, 7.66; N, 9.59.

EXAMPLE 3:
2-Carbethoxy-1-methyl-1,2,4,5-tetrahydro-3,2-benzoxazepine

A solution of 18.5 g. of O-[o-(1-chloroethyl)-phenethyl]-N-carbethoxyhydroxylamine in 130 ml. of ethanol was treated with 3.85 g. of potassium hydroxide in 55 ml. of ethanol according to the procedure described in Example 1. The end product was recovered by distillation collecting the fraction boiling at 115° C/0.1 mm Hg. The fraction boiling at 100° C/0.2 mm Hg which contained the by-product O-(o-vinylphenethyl)-N-carbethoxyhydroxylamine was discarded. There was thus obtained 7.8 g of 2-carbethoxy-1-methyl-1,2,4,5-tetrahydro-3,2-benzoxazepine.

Analysis: Calculated for $C_{13}H_{17}NO_3$: C, 66.38; H, 7.28; N, 5.95. Found: C, 66.01; H, 7.50; N, 5.76.

EXAMPLE 4:
1-Methyl-1,2,4,5-tetrahydro-3,2-benzoxazepine

The compound was obtained by the procedure similar to that of Example 2, using as a starting material the compound of Example 3. Product methyl-1,2,4,5-tetrahydro-3,2-benzoxazepine was isolated as its hydrochloride in a 76 percent yield. Melting point 193°–194° C. The free base, obtained by treatment of an aqueous suspension of the hydrochloride with sodium bicarbonate, followed by extraction with diethyl ether, boiled at 70° C/0.1 mm Hg.

Analysis: Calculated for $C_{10}H_{13}NO.HCl$: Cl, 17.76; N, 7.02. Found: Cl, 17.71; N, 7.13.

EXAMPLE 5:
2-Carbamyl-1,2,4,5-tetrahydro-3,2-benzoxazepine

To a stirred suspension of 1.95 g. (0.0296 mole) of sodium cyanate in 125 ml. of anhydrous toluene, 0.029 mole of hydrogen chloride in toluene was added dropwise at about −10° C. After 2 hours, a solution of 3.1 g. (0.0208 mole) of 1,2,4,5-tetrahydro-3,2-benzoxazepine in 30 ml. of anhydrous toluene was added and stirring was continued at −10° C for 3 hours. The reaction mixture was allowed to stand in a refrigerator overnight and the precipitate was then collected, thoroughly washed with water and recrystallized from 80 percent ethanol, yielding 2.35 g. of 2-carbamyl-1,2,4,5-tetrahydro-3,2-benzoxazepine melting at 172°–173° C. Yield 58.7%.

Analysis: Calculated for $C_{10}H_{12}N_2O_2$: C, 62.50; H, 6.30; N, 14.57. Found: C, 62.20; H, 6.40; N, 14.56.

EXAMPLE 6:
2-Carbamyl-1-methyl-1,2,4,5-tetrahydro-3,2-benzoxazepine

The compound was prepared similarly to the method of Example 5, using 1-methyl-1,2,4,5-tetrahydro-3,2-benzoxazepine was starting material. Yield 60 percent, m.p. 128°–129° C.

Analysis: Calculated for $C_{11}H_{14}N_2O_2$: C, 64.08; H, 6.84; N, 13.56. Found: C, 63.61; H, 7.08; N, 13.51.

EXAMPLE 7:
1,2-Dimethyl-1,2,4,5-tetrahydro-3,2-benzoxazepine

To 1.1 ml. of 99 percent formic acid, 1 g. (0.0061 mole) of 1-methyl-1,2,4,5-tetrahydro-3,2-benzoxazepine and 0.45 ml. of 38 percent formaldehyde were added. After heating the reaction mixture at 60°–70° C. for about 6 hours, the excess of formic acid was distilled off. The residue was alkalinized with sodium carbonate and then extracted several times with diethyl ether. After washing with water and drying, the organic solution was evaporated. The residue was distilled at 60° C/0.1 mm Hg, giving 0.6 g. of 1,2-diemthyl-1,2,4,5-tetrahydro-3,2-benzoxazepine.

Analysis: Calculated for $C_{11}H_{15}NO$: C, 74.58; H, 8.54; N, 7.91. Found: C, 74.81; H, 8.57; N, 7.70.

EXAMPLE 8:
2-Butyl-1-methyl-1,2,4,5-tetrahydro-3,2-benzoxazepine

A mixture of 3.27 g. (0.02 mole) of 1-methyl-1,2,4,5-tetrahydro-3,2-benzoxazepine, 5.5 g. (0.04 mole) of butyl bromide and 3.18 g. (0.03 mole) of sodium carbonate was heated under stirring for 3 hours at 90° C. and for an additional four hours at 120° C. After cooling the reaction mixture was taken up with diethyl ether, and the inorganic residue filtered off. The filtrate was then evaporated in vacuo and the residue rectified by collecting the fraction boiling at 90° C/0.1 mm Hg. Yield 2.3 g. of 2-butyl-1-methyl-1,2,4,5-tetrahydro-3,2-benzoxazepine.

Analysis: Calculated for $C_{14}H_{21}NO$: C, 76.66; H, 9.65; N, 6.39. Found: C, 76.63; H, 9.68; N, 6.44.

EXAMPLE 9:
2-(2-Carbamyloxyethyl)-1,2,4,5-tetrahydro-3,2-benzoxazepine

8 Grams of ethylene oxide was dissolved at room temperature in 80 ml. of methanol. To this solution, 8 mg. of 1,2,4,5-tetrahydro-3,2-benzoxazepine were added. After standing overnight, the reaction mixture was refluxed for one hour and then evaporated in vacuo. The residue was distilled at 120° C/0.1 mm Hg. giving 9.3 g. of 2-(2-hydroxyethyl)-1,2,4,5-tetrahydro-3,2-benzoxazepine. To 2.9 g. of the latter compound in 160 ml. of chloroform, 2.47 g. of sodium cyanate was added, then hydrogen chloride was bubbled therethrough for about 30 minutes under stirring. The reaction mixture was then transferred to a separatory funnel and treated with 90 ml. aqueous of 5 percent sodium hydroxide. The organic layer was separated, washed with a saturated solution of sodium chloride and dried over sodium sulfate. After evaporation of the chloroform solution, the residue was crystallized from diisopropyl ether giving 1.82 g. of 2-(2-carbamyloxyethyl)-1,2,4,5-tetrahydro-3,2-benzoxazepine, m.p. 110°–111° C.

Analysis: Calculated for $C_{12}H_{16}N_2O_3$: C, 61.00; H, 6.82; N, 11.84. Found: C, 60.74; H, 6.93; N, 11.66.

EXAMPLE 10:
2-Guanyl-1,2,4,5-tetrahydro-3,2-benzoxazepine sulfate 1.15 Grams of 1,2,4,5-tetrahydro-3,2-benzoxazepine hydrochloride and 0.25 g. of cyanamide were refluxed in 20 ml. of anhydrous toluene under stirring for 6 hours. The resulting precipitate was filtered off and dissolved in 15 ml. of warm ethanol. After filtering, 0.6 ml. of concentrated sulfuric acid was added to the resulting solution. Diethyl ether was then added, the mixture chilled, and the resulting precipitate was collected to give a yield of 1.4 g. of 2-guanyl-1,2,4,5-tetrahydro-3,2-benzoxazepine sulfate, m.p. 197°–198° C. (from ethanol).

Analysis: Calculated for $C_{10}H_{13}N_3OH_2SO_4$: C, 41.52; H, 5.23; N, 14.52. Found: C, 40.97; H, 6.00; N, 13.83.

EXAMPLE 11:
2-Diethylcarbamyl-1-methyl-1,2,4,5-tetrahydro-3,2-benzoxazepine To a solution of 2.45 g. of 1-methyl-1,2,4,5-tetrahydro-3,2-benzoxazepine and 2.02 g. of triethylamine in 25 ml. of anhydrous benzene was added dropwise 2.17 g. of diethylcarbamylchloride at room temperature. After refluxing for 17 hours, the benzene solution was washed with 2 percent HCl, then with 5 percent NaOH and finally with water. The residue obtained by evaporation of the solvent was distilled at 140° C/0.1 mm Hg giving 2.2 g. of 2-diethylcarbamyl-1-methyl-1,2,4,5-tetrahydro-3,2-benzoxazepine.

Analysis: Calculated for $C_{15}H_{22}N_2O_2$: C, 68.65; H, 8.45; N, 10.67. Found: C, 68.84; H, 8.60; N, 10.47.

EXAMPLE 12:
1-Methyl-2-(3-methyl-2-butenoyl)-1,2,4,5-tetrahydro-3,2-benzoxazepine To 1.55 g. of 3-methyl-2-butenoyl chloride in 15 ml. of dichloromethane, 2.12 g. of 1-methyl-1,2,4,5-tetrahydro-3,2-benzoxazepine in 23 ml. of dichloromethane and 2.02 g. of triethylamine were added dropwise under stirring. The solution was refluxed for about 2 hours and then washed sequentially with aqueous 5 percent HCl, aqueous sodium bicarbonate and water. The residue obtained by evaporation of the solvent was distilled at 145° C/0.2 mm Hg giving 2.3 g. of 1-methyl-2-(3-methyl-2-butenoyl)-1,2,4,5-tetrahydro-3,2-benzoxazepine.

Analysis: Calculated for $C_{15}H_{19}NO_2$: C, 73.44; H, 7.81; N, 5.71. Found: C, 73.60; H, 7.90; N, 5.41.

EXAMPLE 13:
1-Methyl-1,2,4,5-tetrahydro-3,2-benzoxazepine-2-carbonyl chloride A solution of 5.05 g. of 1-methyl-1,2,4,5-tetrahydro-3,2-benzoxazepine and 4.8 ml. of triethylamine in 50 ml. of anhydrous toluene were added to 3.67 g. of $COCl_2$ in 200 ml. of anhydrous toluene at 0°–5° C. The mixture was maintained at room temperature for 6 hours, then heated at 80° C. for 2 hours. After cooling, the organic solution was washed with dilute ammonium hydroxide then with water. After evaporation of the solvent, the residue was distilled at 130° C/0.03 mm Hg. Yield g. 5.2 M.p. 57°–59° C.

Analysis: Calculated for $C_{11}H_{12}ClNO_2$: C, 58.56; H, 5.36; N, 6.21; Cl, 15.72. Found: C, 58.46; H, 6.38; N, 6.36; Cl, 15.54.

EXAMPLE 14:
2-Diallylcarbamyl-1-methyl-1,2,4,5-tetrahydro-3,2-benzoxazepine A solution of 2.6 g. of 88 percent 1-methyl-1,2,4,5-tetrahydro-3,2-benzoxazepine-2-carbonyl chloride in 20 ml. of dichloromethane was added at room temperature to a solution of 2.23 g. of diallylamine in 30 ml. of dichloromethane. The mixture was then refluxed for two hours and after cooling was washed sequentially with aqueous 5 percent HCl, with aqueous sodium bicarbonate and with water. The organic layer was dried over $Na_2SO_4$ and evaporated to dryness. The residue was distilled at 140° C/0.02 mm Hg. Yield 2.3 g.

Analysis: Calculated for $C_{17}H_{22}N_2O_2$: C, 71,34; H, 7.69; N, 9.78. Found: C, 71.02; H, 7.85; N, 10.00.

EXAMPLE 15:
1-Methyl-2-methylcarbamyl-1,2,4,5-tetrahydro-3,2-benzoxazepine A solution of 1.37 g. of methylisocyanate in 10 ml. of diethyl ether was added dropwise to a solution of 1.96 g. of 1-methyl-1,2,4,5-tetrahydro-3,2-benzoxazepine in 30 ml. of diethyl ether under stirring at 0°–5° C. After standing overnight the solution was evaporated to dryness and the oily residue was distilled at 160° C/0.02 mm Hg. Yield 2.41 g.

Analysis: Calculated for $C_{12}H_{16}N_2O_2$: C, 65.40; H, 7.32; N, 12.72. Found: C, 65.52; H, 7.38; N, 12.74.

EXAMPLE 16 TO 25:

The following compounds were prepared according to methods described in previous examples.

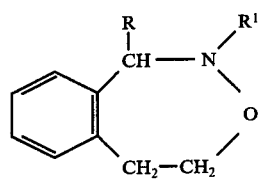

Table 1

| Example No. | R | R¹ | B.P.° C/ mm Hg or M.P.° C (solvent) | Formula | C% Calc. | C% Found | H% Calc. | H% Found | N% Calc. | N% Found |
|---|---|---|---|---|---|---|---|---|---|---|
| 16 | H | CH₃ | 50/0.1 | $C_{10}H_{13}NO$ | 73.58 | 73.14 | 8.03 | 8.31 | 8.58 | 8.22 |
| 17 | CH₃ | CH₂—CH=CH₂ | 80/0.1 | $C_{13}H_{17}NO$ | 76.81 | 76.92 | 8.43 | 8.48 | 6.89 | 6.69 |
| 18 | CH₃ | CO—CH₃ | 86–87 (hexane) | $C_{12}H_{15}NO_2$ | 70.22 | 70.25 | 7.38 | 7.41 | 6.81 | 6.70 |
| 19 | CH₃ | CO-C₆H₂(OCH₃)₃ | 153–55 (ethanol) | $C_{20}H_{23}NO_5$ | 67.21 | 67.54 | 6.49 | 6.53 | 3.92 | 3.86 |
| 20 | H | CO-C₆H₄-Cl | 132–33 (ethanol/ H₂O) | $C_{16}H_{14}ClNO_2$ | 66.80 | 66.93 | 4.90 | 4.78 | 4.87 | 4.67 |

Table 1-continued

| Example No. | R | R¹ | B.P.° C/ mm Hg or M.P.° C (solvent) | Formula | C% Calc. | C% Found | H% Calc. | H% Found | N% Calc. | N% Found |
|---|---|---|---|---|---|---|---|---|---|---|
| 21 | $CH_3$ | CO—⟨phenyl⟩—Cl | 200/0.4 | $C_{17}H_{16}ClNO_2$ | 67.70 | 67.66 | 5.32 | 5.40 | 4.65 | 4.41 |
| 22 | $CH_3$ | CO—N(CH₃)₂ | 89–90 (hexane) | $C_{13}H_{18}N_2O_2$ | 66.64 | 66.42 | 7.74 | 7.79 | 11.96 | 11.88 |
| 23 | $CH_3$ | CO—N⟨piperidyl⟩ | 160/0.02 | $C_{16}H_{22}N_2O_2$ | 70.04 | 70.12 | 8.08 | 8.14 | 10.21 | 10.10 |
| 24 | $CH_3$ | CO—N⟨morpholinyl⟩ | 170/0.02 | $C_{15}H_{20}N_2O_3$ | 65.22 | 65.29 | 7.26 | 7.35 | 10.14 | 10.20 |
| 25 | $CH_3$ | CO—N(CH₂—CH₂—OH)₂ | 180/0.01 | $C_{15}H_{22}N_2O_4$ | 61.20 | 61.32 | 7.54 | 7.56 | 9.52 | 9.60 |

EXAMPLE 26

A.
2-Acetyl-1-methyl-7(8)-nitro-1,2,4,5-tetrahydro-3,2-benzoxazepine

A solution of 30.1 g. of $KNO_3$ in 187 ml. of concentrated sulfuric acid was added at 0° C to 44 g. of 1-methyl-2-acetyl-1,2,4,5-tetrahydro-3,2-benzoxazepine dissolved in 187 ml. of concnetrated sulfuric acid. The mixture was then allowed to stand at room tempratue for 90 minutes, then was poured onto about one kg. of crushed ice under stirring. After extraction with 3 liters of dichloromethane, the organic solution was washed with aqueous sodium bicarbonate, dried over sodium sulfate then evaporated to dryness. The residue was stirred with one liter of diisopropyl ether. The resulting insoluble solid was then collected on a filter and washed with diisopropyl ether. After crystallization from ethanol, 37 g. of 1-methyl-2-acetyl-7(8)-nitro-1,2,4,5-tetrahydro-3,2-benzoxazepine was obtained, m.p. 196°–7° C.

Analysis: Calculated for $C_{12}H_{14}N_2O_4$: C, 57.59; H, 5,64; N, 11.19. Found: C, 57.25; H, 5,76; N, 11.12.

B.
2-Acetyl-1-methyl-8(7)-nitro-1,2,4,5-tetrahydro-3,2-benzoxazepine

The diisopropyl ether extract of preceding procedure A was concentrated to 300 ml. and chilled with an ice bath. The precipitate which formed was collected on a filter and crystallized from diisopropyl ether. Yield 3.5 g. of 1-methyl-2-acetyl-8(7)-nitro-1,2,4,5-tetrahydro-3,2-benzoxazepine. M.p. 106°–7° C.

Analysis: Calculated for $C_{12}H_{14}N_2O_4$: C, 57.59; H, 5.64; N, 11.19. Found: C, 57.92; H, 5.81; N, 11.65.

EXAMPLE 27

1-Methyl-7(8)-nitro-1,2,4,5-tetrahydro-3,2-benzoxazepine

Fifteen grams of 2-acetyl-1-methyl-7(8)-nitro-1,2,4,5-tetrahydro-3,2-benzoxazepine was heated on a steam bath for 4 hours with 300 ml. of 20 percent HCl. After evaporation under reduced pressure, the residue was taken up with aqueous sodium bicarbonate. The mixture was extracted with dichloromethane and the organic phase was evaporated to dryness. The residue after crystallization from diisopropyl ether melts at 82°–3° C. Yield 11.6 g.

Analysis: Calculated for $C_{10}H_{12}N_2O_3$: C, 57.67; H, 5.81; N, 13.45. Found: C, 57.80; H, 5.85; N, 13.46.

EXAMPLE 28

1-Methyl-2-diphenylcarbamyl-7(8)-nitro-1,2,4,5-tetrahydro-3,2-benzoxazepine

The compound was prepared according to the procedure described in Example 11, utilizing as the starting compounds 1-methyl-7(8)-nitro-1,2,4,5-tetrahydro-3,2-benzoxazepine and diphenylcarbamyl chloride. Yield 83 percent, m.p. 157°–8° C. (from ethanol).

Analysis: Calculated for $C_{23}H_{21}N_3O_4$: C, 68,48; H, 5.25; N, 10.41. Found: C, 67.90; H, 5,48; N, 10.26.

EXAMPLE 29

2-Carbamyl-1-methyl-7(8)-nitro-1,2,4,5-tetrahydro-3,2-benzoxazepine

The compound was prepared according to the procedure described in Example 5 for 2-carbamyl-1,2,4,5-tetrahydro-3,2-benzoxazepine by using 4.03 g. of 1-methyl-7(8)-nitro-1,2,4,5-tetrahydro-3,2-benzoxazepine as starting material. Yield 60 percent. M.p. 200°–2° C. (from ethanol).

Analysis: Calculated for $C_{11}H_{13}N_3O_4$: C, 52.60; H, 5.22; N, 16.73. Found: C, 52.35; H, 5.28; N, 16.74.

EXAMPLE 30

2-Acetyl-7(8)-amino-1-methyl-1,2,4,5-tetrahydro-3,2-benzoxazepine

A solution of 25.2 g. of 2-acetyl-1-methyl-7(8)-nitro-1,2,4,5-tetrahydro-3,2-benzoxazepine in 2 liters of ethanol was hydrogenated at room temperature and atmospheric pressure by using 2.5 g. of 5 percent palladiated charcoal as a catalyst. After three hours, when the theoretical amount of hydrogen had been consumed, the catalyst was filtered off and the solution evaporated to dryness. The residue was crystallized from diisopropyl ether. Yield 18.95 g. m.p. 116°–7° C.

Analysis: Calculated for $C_{12}H_{16}N_2O_2$: C, 65.42; H, 7.32; N, 12.72. Found: C, 65.58; H, 7.50; N, 12.51.

EXAMPLES 31 and 32

By operating according to the method described in Example 30, the following compounds were prepared by using the corresponding nitro derivatives as the starting materials.

(31) 7(8)-Amino-2-carbamyl-1-methyl-1,2,4,5-tetrahydro-3,2-benzoxazepine. Yield 87 percent. M.p. 189°–90° C. (from benzene).

(32) 7(8)-Amino-2-diphenylcabamyl-1-methyl-1,2,4,5-tetrahydro-3,2-benzoxazepine. Yield 52 percent. M.p. 89°–90° C.

EXAMPLE 33

7(8)-Acetamido-2-carbamyl-1-methyl-1,2,4,5-tetrahydro-3,2-benzoxazepine

A solution of 0.86 ml. of acetyl chloride in 5 ml. of dichloromethane was added dropwise at room temperature to a solution of 2.66 g. of 7(8)-amino-2-cabamyl-1-methyl-1,2,4,5-tetrahydro-3,2-benzoxazepine and 2.1 ml. of triethylamine in 30 ml. of dichloromethane. After standing at room temperature for 4 hours, 500 ml. of dichloromethane was added to the solution and after washing with water and drying over sodium sulfate, the organic solvent was removed by distillation. The residue was crystallized from ethyl acetate. Yield 1.4 g. M.p. 205°–6° C.

Analysis: Calculated for $C_{13}H_{17}N_3O_3$: C, 59.34; H, 6.51; N, 15.94. Found: C, 59.29; H, 6.67; N, 16.06.

EXAMPLE 34

2-Acetyl-7(8)-chloro-1-methyl-1,2,4,5-tetrahydro-3,2-benzoxazepine 16.3 Grams of 2-acetyl-7(8)-amino-1-methyl-1,2,4,5-tetrahydro-3,2-benzoxazepine was dissolved in 170 ml. of aqeous 15 percent HCl and 5.5 g. of sodium nitrite in 55 ml. of $H_2O$ was added to the solution at 0° C. A mixture of 49.5 g. of $CuSO_4.5H_2O$ and 12.6 g. of NaCl in 158 ml. of water was heated to 90°–100° C. and 6.85 g. of sodium hydroxide and 10 g. of $Na_2S_2O_5$ in 90 ml. of water were added to the resulting solution. After cooling at room temperature the solid which precipitated was dissolved in 295 ml. of aqueous 15 percent HCl. The solution containing the so-prepared diazo compound was then added dropwise at room temperature under stirring to the acidic CuCl solution prepared as described above. The so-obtained mixture was then extracted three times with diethyl ether and the combined organic layers were washed with aqueous sodium bicarbonate. The dried organic phase, upon evaporation gave a solid residue which after crystallization from diisopropyl ether melted at 89°–90° C. Yield 75 percent.

Analysis: Calculated for $C_{12}H_{14}ClNO_2$: C, 60.14; H, 5.89; N, 5.84; Cl, 14.78. Found: C, 60.26; H, 5.98, N, 5.81, Cl, 14.74.

EXAMPLE 35

7(8)-chloro-1-methyl-1,2,4,5-tetrahydro-3,2-benzoxazepine

The compound was prepared by following the procedure described for 1-methyl-7(8)-nitro-1,2,4,5-tetrahydro-3,2-benzoxazepine in Example 27 by using 2-acetyl-7(8)-chloro-1-methyl-1,2,4,5-tetrahydro-3,2-benzoxazepine as the starting compound. Yield 93 percent. B.p. 95° C/0.03 mm Hg. M.p. 58°–60° C.

Analysis: Calculated for $C_{10}H_{12}ClNO$: C, 60.75; H, 6.12; N, 7.09; Cl, 17.94. Found: C, 60.91; H, 6.28; N, 7.18; Cl, 18.05.

EXAMPLE 36

2-Cabamyl-7(8)-chloro-1-methyl-1,2,4,5-tetrahydro-3,2-benzoxazepine

By operating according to the procedure described in Example 5 the title compound was obtained in a 50 percent yield by using 3 g. of 7(8)-chloro-1-methyl-1,2,4,5-tetrahydro-3,2-benzoxazepine as the starting compound. M.p. 160°–2° C. from ethanol.

EXAMPLE 37

7(8)-Chloro-1-methyl-2-diphenylcarbamyl-1,2,4,5-tetrahydro-3,2-benzoxazepine

The compound was prepared similarly to the method described in Example 28 by using 7(8)-chloro-1-methyl-1,2,4,5-tetrahydro-3,2-benzoxazepine and diphenylcarbamyl chloride as the starting compounds. M.p. 164°–6° C. from methano. Yield 64 percent.

EXAMPLE 38

(o-Acetoxymethyl)phenethyl bromide

A solution of 66 g. of o-(2-bromoethyl)benzaldehyde in 1.2 1. of ethanol and 310 ml. of water was shaken with hydrogen at room temperature and atmospheric pressure in the presence of 7 g. of $PtO_2$ and of some crystals of $Fe_2So_4.7 H_2O$ until the uptake of one molar equivalent of hydrogen was completed. The mixture was then filtered through charcoal and the ethanol was evaporated. The residue was extracted several times with diethylether. The combined extracts were dried over $Na_2SO_4$ and concentrated. The residue was suspended in 200 ml. of hexane and diisopropyl ether (1:1.5) and cooled to yield 52.5 g. (78.8%) of (o-hydroxymethyl)-phenethyl bromide, m.p. 61°–2° C. The compound was acetylated by treatment with excess acetic anhydride on a steam bath for 2 hours. The final compound was recovered by distilling at 110° C/0.2 mm Hg.

EXAMPLE 39

O-[(o-hydroxymethyl)phenethyl]-N-carbethoxy hydroxylamine

A mixture of 75.2 g. crude potassium N-hydroxyurethane (0.33 mole) and 35.45 g. of N-hydroxyurethane (80 percent purity, 0.27 mole) and 280 ml. of dimethylformamide was stirred at room temperature for 10 minutes. A solution of 70 g. (0.27 mole) (o-acetoxymethyl)-phenethyl bromide in 58 ml. of dimethylformamide was then added dropwise over a period of 15 minutes. Stirring was continued for about one hour at 75° C (final pH=7). The solvent was evaporated in vacuo and the residue was taken up with 3 l. of diethyl ether. After washing with aqueous 5 percent NaOH then with water until neutral, the solution was dried over anhydrous sodium sulfate and concentrated. The oily residue was introduced in a bulb and heated gradually to 150° C/0.5 mm H. to eliminate the by-produce o-vinylbenzyl alcohol acetate and the excess of N-hydroxyurethane. The residue of the distillation weighing 36.7 g. containing about 85 percent of O-(o-acetoxymethylphenethyl)-N-carbethoxyhydroxylamine was dissolved in 320 ml. of ethanol and 138 ml. of aqueous NaOH was added, leaving the solution at room temperatue for 16 hours. The solvent was then evaporated in vacuo and the residue dissolved in diethyl ether. After washing with water, the organic phase was dried over sodium sulfate and concentrated, yielding 27 g. (88 percent) of crude O-(o-hydroxymethylphenethyl)-N-carbethoxyhydroxylamine. A sample of the pure title compound was obtained by distilling at 180° C/0.1 mm Hg.

EXAMPLE 40

O-[(o-Bromomethyl)phenethyl]-N-carbethoxy hydroxylamine

A solution of 53.6 g. (0.22 mole) of O-(o-hydroxymethylphenethyl)-N-carbethoxyhydroxylamine in 310 ml. of dichloromethane was added dropwise to 1200 ml. of the same solvent saturated at 0° C. with dry hydrogen bromide. After the addition, the solvent was again saturated with hydrogen bromide and left for 1 hour at room temperature. After evaporation of the solvent, the residue was triturated in hexane, giving 60 g. of O-(o-bromomethyl-phenethyl)-N-carbethoxyhydroxylamine, m.p. 70°–72° C.

EXAMPLE 41 o-[(1-Hydroxyethyl)phenethyl] bromide

To a diethyl ether solution (1000 ml.) containing the Gringnard reagent prepared from 13.6 g. of magnesium and 38 ml. of methyl iodide, an amount of 85.2 g. of o-(2-bromoethyl)benzaldehyde in 800 ml. of anhydrous diethyl ether was added. After five hours at 0° C., the solution was treated at 10°–14° C with 320 mil. of aqueous 20 percent ammonium chloride. The organic layer, after washing with water and drying, was evaporated, giving 70 g. of crude o-(l-hydroxyethyl)phenethyl bromide, m.p. 50°–1° C (crystallized from diisopropyl ether:hexane 1:1)

EXAMPLE 42 o-[(l-Hydroxyethyl)phenethyl]-N-carbethoxy hydroxylamine

To a mixture of 340 g. of 60 percent potassium N-hydroxyurethane and 150 ml. of N-hydroxyurethane in 1200 ml. of anhydrous dimethylformamide was added dropwise 277 g. of o-(l-hydroxyethyl)phenethyl bromide in 450 ml. of anhydrous dimethylformamide. The mixture was kept for 1 hour at 70° C., and then dimethylformamide was distilled off to about half volume. The residue was poured into 2000 ml. of water and extracted several times with diethyl ether. The combined organic layers were washed with aqueous 5 percent sodium hydroxide, then with water. Upon evaporation of the solvent, 227 g. of crude O-[o-(l-hydroxyethyl)phenethyl]-N-carbethoxyhydroxylamine was obtained. A pure sample of the compound boiled at 180°–90° C/0.2 mm Hg.

EXAMPLE 43

O-[o-(l-Chloroethyl)phenethyl]-N-carbethoxy hydroxylamine

The compound obtained according to Example 42 was transformed into the corresponding chloro derivative by operating in the manner of Example 40 but using hydrogen chloride instead of hydrogen bromide. The final crude compound was used as such to prepare 2-carbethoxy-1-methyl-1,2,4,5-tetrahydro-3,2-benzoxazepine.

The compounds of the invention have anti-inflammatory and central nervous system activity. Their action on the central nervous system is essentially characterized by hypnotic, sedative or myorelaxing effects. In some cases these compounds also display an anxiety-relieving effect.

In representative operations, the compounds of Examples 7, 11, 15, 16 and 24, when tested in rats against carrageenin-induced edema at a dose of 100 mg/kg per os, (which corresponds to about one-tenth to about one-fifth of the $LD_{50}$ value) provided a percent decrease of the carrageenin-induced edema ranging from about 25 to about 30.

| ANTINFLAMMATORY ACTIVITY Carrageenin-induced edema test | | |
|---|---|---|
| Compound of Example No. | Dose mg/kg p.o. | % Decrease of of the edema |
| 7 | 100 | 30 |
| 11 | 100 | 31 |
| 15 | 100 | 31.5 |
| 16 | 100 | 30.5 |
| 24 | 100 | 32 |

Decreasing the spontaneous activity in mice after intraperitoneal administration of an effective amount of the compounds was taken as a measure of the sedative effect, while impairment of motor coordination and righting reflex were related to hypnotic properties. The myorelaxing characteristics were evaluated by considering the body tone, while the anxiety-relieving effect was measured on the basis of the inhibition of the secondary conditioned avoidance response. In representative operations, amounts from about 10 to about 100 mg/kg. i.p. of the compounds of Examples 4, 6, 9, 16 and 18 were found to be effective on the above-mentioned parameters as measures of the stated central nervous system activity.

| ACTIVITY ON C.N.S. $ED_{50}$mg/kg i.p. in mice | | | | |
|---|---|---|---|---|
| Compound of Example No. | Spontaneous activity | Impairment of motor coordination and righting reflex | Body tone | Secondary conditioned avoidance response |
| 4 | 100 | 60 | 20 | 60 |
| 6 | 60 | 60 | 80 | 15 |
| 9 | 100 | 100 | 300 | 30 |
| 16 | 100 | 120 | 10 | 40 |
| 18 | 100 | 60 | 200 | 60 |

The favorable biological characteristics of the inventive compounds are couplied with a relatively low toxicity, since the $LD_{50}$ in mice for the compounds of Examples 6, 7, 9, 11, 12, 15–17 and 24 was found to be higher than 500 mg/kg. i.p.

We claim:

1. A benzoxazepine compound represented by the formula

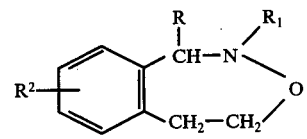

wherein R represents hydrogen or lower alkyl, $R^1$ represents a member of the group consisting of hydrogen; lower alkyl; lower alkenyl; and hydroxy lower alkyl;

and $R^2$ may be in position 7 or 8 of the benzoxazepine ring and represents hydrogen, nitro, amino, acetamino or halo.

2. A compound as claimed in claim 1 wherein R represents hydrogen or methyl; $R^1$ represents hydrogen or lower alkyl and $R^2$ represents hydrogen, nitro, amino, acetamino or chloro.

3. A compound as claimed in claim 1 wherein R is hydrogen or methyl, $R^1$ is hydrogen or methyl, and $R^2$ is hydrogen.

4. The compound of claim 2 which is 1,2-dimethyl-1,2,4,5-tetrahydro-3,2-benzoxazepine.

5. The compound of claim 2 which is 2-methyl-1,2,4,5-tetrahydro-3,2-benzoxazepine.

6. The compound of claim 2 which is 1,2,4,5-tetrahydro-3,2-benzoxazepine.

7. The compound of claim 2 which is 1-methyl-1,2,4,5-tetrahydro-3,2-benzoxazepine.

* * * * *